United States Patent [19]
Brewster et al.

[11] Patent Number: 5,960,337
[45] Date of Patent: Sep. 28, 1999

[54] METHOD FOR RESPONDING TO AN EMERGENCY EVENT

[75] Inventors: Beth S. Brewster, Livermore; John F. Schipper, Palo Alto; James M. Janky, Los Altos, all of Calif.

[73] Assignee: Trimble Navigation Limited, Sunnyvale, Calif.

[21] Appl. No.: 08/822,580

[22] Filed: Mar. 20, 1997

Related U.S. Application Data

[63] Continuation of application No. 08/299,844, Sep. 1, 1994, abandoned.

[51] Int. Cl.$^6$ .................................................. G01S 1/08
[52] U.S. Cl. ......................... 455/404; 342/386; 600/523
[58] Field of Search .......................... 455/404; 342/386, 342/357; 600/523; 128/904

[56] References Cited

U.S. PATENT DOCUMENTS

| | | | |
|---|---|---|---|
| 3,864,522 | 2/1975 | DeKozan et al. | 179/5.5 |
| 3,925,763 | 12/1975 | Wadhwani et al. | 340/164 R |
| 4,004,577 | 1/1977 | Sarnoff . | |
| 4,141,006 | 2/1979 | Braxton | 340/505 |
| 4,176,254 | 11/1979 | Tuttle et al. | 179/5 R |
| 4,237,344 | 12/1980 | Moore | 179/2 A |
| 4,463,357 | 7/1984 | MacDoran | 343/460 |
| 4,649,385 | 3/1987 | Aires et al. | 379/57 |
| 4,878,236 | 10/1989 | Ray et al. | 379/37 |
| 4,931,780 | 6/1990 | LaMont et al. | 340/691 |
| 4,979,206 | 12/1990 | Padden et al. | 379/67 |

(List continued on next page.)

OTHER PUBLICATIONS

Christopher O'Malley, "Electronics as Your Copilot," pp. 66–69, Popular Science, Sep. 1991.

Tom Logsdon, "The Navstar Global Positioning System," pp. 1–91, Van Nostrand Reinhold 1992.

"Navstar GPS Space Segment/Navigation User Interfaces," Interface Control Document GPS(200), No. ICD–GPS–200, Rockwell International, Satellite Systems Division, Rev. B–PR, IRN–200B–PR–001, Apr. 16, 1993.

Primary Examiner—William Cumming
Attorney, Agent, or Firm—John F. Schipper

[57] ABSTRACT

A method for improving the provision of emergency assistance services for an emergency site. An observer of an emergency event contacts an Emergency Assistance Services (EAS) operator, using a telephone to describe the type of emergency event and any special circumstances present. The EAS operator also receives the present location of the observer, using a location determination system that is connected to the telephone used by the observer. The EAS operator is provided with an electronic map showing the location of the observer and the location of at least one available EAS responder for the type of emergency event that has occurred. The EAS operator determines whether a given EAS responder has the equipment and/or trained personnel required to respond to the emergency event and, from a group of EAS responders who do so qualify, selects an EAS responder who is estimated to be able to reach the emergency site in the shortest time. The selected EAS responder is assigned to respond to the emergency event, and the EAS operator optionally monitors the EAS responder to verify that this responder has reached the emergency site. If the assigned EAS responder does not reach the emergency site, the EAS operator optionally and promptly assigns another EAS responder to the emergency event. The LD system can be a Satellite Positioning System, such as GPS or GLONASS, or can be an FM subcarrier system.

20 Claims, 5 Drawing Sheets

U.S. PATENT DOCUMENTS

| | | | |
|---|---|---|---|
| 5,012,507 | 4/1991 | Leighton et al. | 379/37 |
| 5,021,794 | 6/1991 | Lawrence | 342/457 |
| 5,045,861 | 9/1991 | Duffett-Smith | 342/457 |
| 5,055,851 | 10/1991 | Sheffer | 342/457 |
| 5,077,788 | 12/1991 | Cook et al. | 379/142 |
| 5,091,930 | 2/1992 | Shapiro | 379/39 |
| 5,095,531 | 3/1992 | Ito | 455/33 |
| 5,109,399 | 4/1992 | Thompson | 379/45 |
| 5,161,180 | 11/1992 | Chavous | 379/45 |
| 5,164,979 | 11/1992 | Choi | 379/40 |
| 5,173,710 | 12/1992 | Kelley et al. | 342/463 |
| 5,218,367 | 6/1993 | Sheffer et al. | 342/457 |
| 5,270,708 | 12/1993 | Kamishima | 340/995 |
| 5,305,370 | 4/1994 | Kearns et al. | 379/45 |
| 5,311,569 | 5/1994 | Brozovich et al. | 379/45 |
| 5,334,974 | 8/1994 | Simms et al. | 340/990 |
| 5,347,567 | 9/1994 | Moody et al. | 379/45 |
| 5,355,140 | 10/1994 | Slavin et al. | 342/386 |
| 5,388,147 | 2/1995 | Grimes | 379/59 |
| 5,414,629 | 5/1995 | Inoue | 364/444 |
| 5,486,822 | 1/1996 | Tenmoku et al. | 340/995 |
| 5,515,285 | 5/1996 | Garrett, Sr. et al. | 364/460 |
| 5,537,460 | 7/1996 | Holliday, Jr. et al. | 379/59 |

Incident: Structure Fire
Needed:
1. Fire fighting personnel
2. Fire fighting equipment
3. SCBAs
4. Gurney(s)
5. Oxygen

FIG. 3A

Incident: Vehicle Accident/Injury
Needed:
1. First Aid personnel
2. Fire Fighting equipment
3. Gurney(s)
4. Medicines
5. Blood units

FIG. 3B

Incident: Shooting/Injury
Needed:
1. First Aid personnel
2. Gurney(s)
3. Medicines
4. Blood units

FIG. 3C

Incident: Toronado
Needed:
1. Fire fighting personnel
2. First Aid personnel
3. Gurney(s)
4. Structure movers
5. Medicines

FIG. 3D

METHOD FOR RESPONDING TO AN EMERGENCY EVENT

This application is a Continuation of U.S. Ser. No. 08/299,844, filed Sep. 1, 1994 now abandoned.

FIELD OF THE INVENTION

This invention relates to provision of emergency assistance for a telephone caller and to monitoring of progress for the selected responder for the emergency.

BACKGROUND OF THE INVENTION

As the number of telephone calls seeking emergency assistance increases in a given region, some problems have surfaced. A caller seeking emergency assistance (referred to as an "EA caller" for convenient reference) is often under great stress and may not be able to give an accurate description of the location of the emergency site. The emergency service call operator who receives such a call may be unfamiliar with the locations of each emergency assistance service ("EAS") agency that can properly respond to the call and may be unable to determine which of these agencies is available and can respond most quickly to that location. Recently, in a Northern California community, a car overturned and caught fire, trapping the driver inside. A passerby immediately called "911", reported the accident, and requested immediate dispatch of a fire engine and crew to put out the fire and administer first aid and emergency services to the trapped driver. The 911 service operator called a fire engine crew on the other side of town, not realizing that the closest available fire engine crew was less than two miles from the accident scene along a low-traffic road. When the summoned fire engine crew arrived 15 minutes later, in part because the location of the accident scene was wrongly reported, the driver had perished from the flames, not from any injuries sustained in the accident itself. An approach is needed that removes the factor of EAS operator ignorance in prompt response to a 911 call for emergency assistance.

Another problem is manifested where, in response to an EA call requiring at most one responder, two, three or more EAS responders arrive at an emergency site in response to the call. Another problem arises in lack of means for monitoring whether the assigned EAS responder has, in fact, arrived at the emergency site and whether additional assistance and/or equipment is needed at that site.

Workers in the field of EA response systems have from time to time proposed systems that address some, but not all, of these problems.

In U.S. Pat. No. 3,864,522, DeKozan et al disclose a system for automatically determining the location of a telephone used to make a call to an emergency station (ES). When the ES receives a phone call, the ES telephone transmits a low frequency interrogation signal (at about 1 kHz), requesting the location of the caller's phone. This interrogation signal is answered by a response, using a binary or two-tone sequence of pulses indicating the location of the caller's phone. This response signal is received and decoded, and the caller's phone location is stored for subsequent use for an emergency response. This system requires two-way response: transmission of an interrogation signal, and transmission in the reverse direction of a response signal. The caller's phone location must be unchanging so that a static location can be stored thereat, for response to an interrogation signal. The person responding to the emergency call must then rely on his or her personal knowledge to dispatch the correct responder to answer the emergency call.

A security alarm system for detecting and signalling the presence of abnormal or emergency conditions in a specified area is disclosed by Wadhwani et al in U.S. Pat. No. 3,925,763. The system relies on placement of sensors that respond to the occurrence of specific events. When such an event does occur, a coded signal, including the location and event type that has occurred, is sent along a telephone or other signal-carrying line to a central station, where the signal is decoded and an appropriate response is determined. The system also includes circuitry that interrogates the sensors and lines to determine whether any component of the system is not operational.

Tuttle et al, in U.S. Pat. No. 4,176,254, disclose a roadside telephone system for emergency calls to a central station to obtain emergency assistance. Each roadside telephone module includes a handset, transmitter, receiver, and a sequence of switches or buttons that request a response by a particular type of emergency responder, such as fire truck, police, ambulance or auto road service. The phone handset or these switches may be used to inform the central station of the type of emergency, but the caller must use the handset to verbally inform the central station of the caller's location—assuming that the caller knows the location. A timing circuit automatically disconnects the phone connection after three minutes if the handset is still off-hook, to conserve electrical power.

U.S. Pat. No. 4,237,244, issued to Moore, discloses a rapid response communications system for use in a hospital or other large health care facility. The system includes personal locators, to be used by specified health care personnel, such as doctors, nurses, interns, orderlies, etc. in the facility. When a health care person enters a room, that person presses a button whenever that person enters a room at the facility, using a panel of buttons beside the entrance to the room. This panel includes one button for each type of health care personnel: doctor, registered nurse, practical nurse, technician, aide, emergency responder. Pressing a panel button causes a central display, located on one or more floors of the facility, to indicate that a health care person of that type has entered that room. When the health care person leaves the room, that person presses the same button or takes some other action to indicate that that person has left that room, for purposes of the central display. It is unclear what action is taken to indicate that, say, more than one doctor is present in a given room or that one of these doctors has just left the room. When a patient or other person needs the assistance of a particular type of health care person, the patient contacts the central station, which locates an available health care person using the information shown on the central display.

Ray et al disclose an automatic emergency caller locator system in U.S. Pat. No. 4,878,236. The system, which is apparently intended to be part of a roadside telephone module, senses when a phone call is being placed to a 911 number and turns on a flashing light or strobe to allow an emergency responder to more easily locate the caller. An authorized person resets the telephone module and deactivates the light, for example by dialing a predetermined phone number. This system relies upon the caller to verbally state an approximately correct location for the emergency responder. A similar system, which turns on an exterior visual or audible alarm that can be easily sensed when a 911 call is made from a house or other building, is disclosed in U.S. Pat. No. 4,931,780, issued to LaMont et al, and in U.S. Pat. No. 5,012,507, issued to Leighton et al.

A personal locator for emergency situations, to be worn by a child or other person to be located, is disclosed by Lawrence in U.S. Pat. No. 5,021,794. The locator responds to receipt of a selected locator signal, such as a particular frequency or combination of frequencies, by transmitting a characteristic UHF response signal that can be located by one or more tracking vehicles, using signal triangulation. A parent or other person who needs to locate the person wearing this locator device transmits a selected digital pulse code over a telephone line, and a non-directional UHF locator signal is transmitted to cause a response signal to be transmitted by the locator device. A tracking vehicle can be given additional information, such as general appearance, gender, age, etc., concerning the person to be located, by radiowave signals.

In U.S. Pat. No. 5,077,788, Cook et al disclose a system for processing calls for emergency assistance, in which the telephone number of the phone caller is automatically identified and used to retrieve information stored in a database. The caller is patched through to the appropriate emergency response agency, and relevant information in the database (e.g., address of the calling station, structure in which the calling station is located, if any) is forwarded to that agency for use in responding to the call for assistance. Optional validation of the caller's phone number is available, for use in screening such calls.

Enhancement of an emergency response system is disclosed in U.S. Pat. No. 5,091,930, issued to Shapiro. This system incorporates an ancillary radiowave subsystem as an alternate communication link between the caller for emergency assistance and the emergency response central station. This subsystem is used to detect whether telephone line interference is present and to provide the caller with an alternative means of communicating with the central station.

Thompson, in U.S. Pat. No. 5,109,399, discloses a computer-based emergency response system in which, upon receipt of a call for emergency assistance at a central station, a map is automatically displayed showing the caller's location at the same time that the voice message is being received. The voice information and/or map information can optionally be communicated to an emergency responder agency, for use in responding to the call. This system does not determine availability of a responder agency or provide an estimate of the time required for response. Location of the caller must be provided by the caller or by identification of the number for a telephone at a fixed location.

A call interceptor for emergency assistance calls that identifies the phone number of location of the source of the call is disclosed by Chavous in U.S. Pat. No. 5,161,180. When a 911 number is dialed from a phone that is part of the network, a subsidiary device interrogates the caller's phone, obtains the phone number, searches a database on phone numbers, and provides the telephone phone number and location of the caller's phone to an emergency response central station. If a response to the interrogation signal is not received, the system uses an alternate route to interrogate the caller's phone.

In U.S. Pat. No. 5,218,367, Sheffer et al disclose a vehicle tracking system that uses a conventional cellular telephone network to report the occurrence of an emergency or of certain other kinds of abnormal events. Special purpose sensors placed on the vehicle sense the occurrence of a specified class of "events" and transmit an emergency message, without human intervention, over the cellular phone, which is preferably concealed on the vehicle. The message transmitted can include information on the type of emergency or abnormal event, vehicle identification, cellular phone zone, and signal strength information. No information directly identifying the vehicle location is included.

U.S. Pat. No. 5,305,370, issued to Kearns et al, discloses a handheld transmitter that enhances use of an emergency assistance system. If a person in need of emergency assistance cannot reach a telephone, this person uses the handheld unit to activate a base unit nearby that places the call and provides two-way voice communication between the caller and an emergency response central station. The base unit would normally be located in the caller's home or place of business and could be used by a person who is injured, disabled or otherwise unable to physically move to and use a conventional telephone. This device can also be used to transmit a silent alarm if a robbery or other similar event is taking place.

Brozovich et al, in U.S. Pat. No. 5,311,569, discloses a phone line-based emergency assistance system that can obtain information on a phone used to make a 911 call, even if the caller is subsequently unable to respond. This includes provision of Automatic Number Identification (ANI) for, and the address of, the caller phone, along with other information contained in a database, such as the building and/or floor and/or section of the floor where the caller phone is located. The information is then optionally displayed at an emergency response central station.

These inventions provide means for obtaining information on the EA caller's location for a limited class of telephones, such those that have a fixed location that can be entered in a static database or those that belong to a special network. What is needed is a system that provides location information for any telephone, mobile or fixed-location.

Also needed is a system that provides means for subsequently monitoring the EAS responders actions, such as arrival at the emergency site, and means for assigning one or more additional EAS responders in light of subsequent developments.

SUMMARY OF THE INVENTION

These needs are met by the invention, which combines a standard telephone handset with a GPS antenna and GPS receiver/processor, an interface between the phone handset and the receiver/processor, and a database and map display, among other things. When a 911 or other EAS call is made, the responding EAS operator activates two communication channels, a first channel for standard voice messages and a second channel for interrogating the GPS receiver/processor to determine the present location of the EA caller or observer. It is assumed that the EA caller is located near the site of the emergency. The EAS operator records information on the type and location of the emergency event from the caller and, simultaneously, receives additional—and more accurate—present location coordinates for the EA caller, displayed on a screen in an electronic map if desired. Depending upon the type of emergency reported, the EAS operator calls up an appropriate database for available responders to that type of emergency, arranged in order of their distance from the emergency site.

The EAS operator then contacts one, two or three of the closest available responders, gives them the details, and verbally or electronically gives the responders the location coordinates of the emergency site. Optionally, each responder queried can quickly estimate, for the 911 service operator, the time required to reach the emergency site, based upon distance from the responder, time of day, and other factors, using a separate database provided for each responder. The EAS operator can then assign one available responder that can reach the emergency site in the (estimated) shortest time to respond to the emergency. If, for whatever reason, the assigned responder subsequently finds that it cannot reach the emergency site, the assigned responder promptly contacts the EAS operator, who calls up the database and quickly (re)assigns another responder for that emergency.

The invention removes or minimizes the effects of several possible errors or mishaps that can occur in such a situation: (1) an error in emergency site location reported by the EA caller; (2) an error by the EAS operator in choice of a responder that can respond in the shortest time; (3) an error by the EAS operator in the proper emergency responders to be contacted; (4) an error by the EAS operator in assigning more than one responder to respond to the event; and (5) occurrence of a subsequent event, such as an accident or blocked access route, experienced by the originally assigned EAS responder enroute to the emergency site.

The invention provides the telephone handset, used by the caller for EAS requests, with an SATPS antenna and receiver/processor that can, through an interface, report the location coordinates of the EA caller. If the phone handset is stationary, as in a public pay phone or phone in a private home, the SATPS equipment can be replaced by a simpler device that automatically transmits the known coordinates of this stationary handset whenever the 911 phone number is dialed and a connection is made. Where the phone used by the EA caller is not stationary but is mobile, SATPS or a similar land-based location determination system (e.g., a Loran-C or FM sub-carrier system) should be used to determine the EA caller's present location

BRIEF DESCRIPTION OF THE DRAWINGS

FIGS. 3A, 3B, 3C and 3D illustrate lists of equipment and trained personnel that may be needed to respond to particular emergencies.

DESCRIPTION OF BEST MODES OF THE INVENTION

Figure 1:
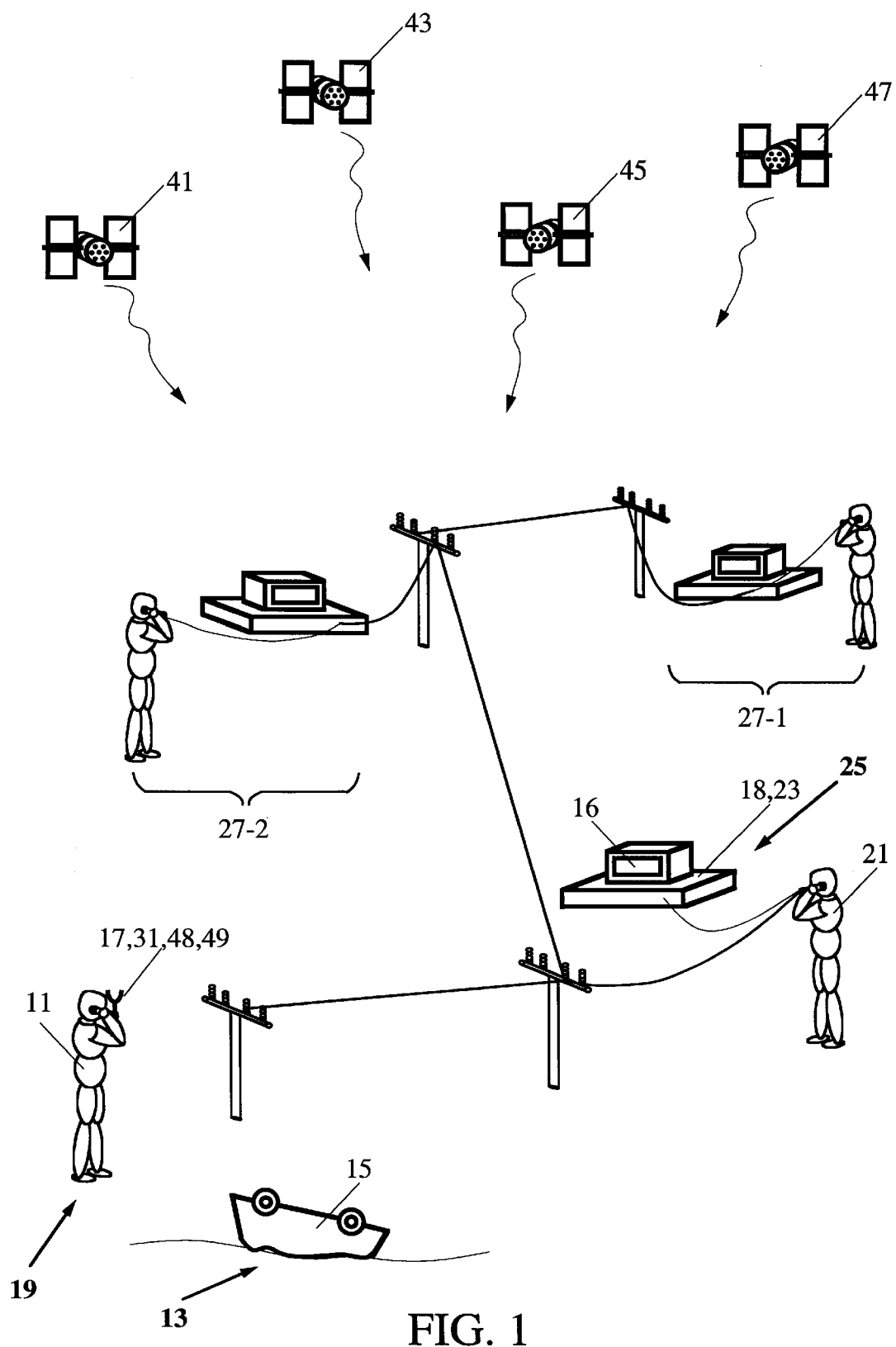
FIGS. 1 and 2 illustrate use of the invention in one class of emergency situations (not drawn to scale), using a Satellite Positioning System (SATPS) and an FM subcarrier system, respectively, for determination of the present location of the emergency incident observer.

FIG. 1 illustrates use of the invention in one embodiment. An observer 11 observes or experiences an incident that creates an emergency at a site 13. The incident may involve a vehicle or vessel 15, as shown in FIG. 1, or may involve another type of incident. The observer 11 uses an available telephone 17 to contact an EAS operator 21 and associated EAS response system 23 at another site 25. The telephone 17 used by the observer may be a fixed location phone, such as a pay telephone or a conventional phone installed in a home or business structure, or may be a mobile phone, such as a mobile cellular telephone. In a first embodiment, the telephone 17 is configured so that, if an EAS agency number such as 911 is dialed on that phone, that phone uses a control signal channel to simultaneously transmit the present location of the phone 17 to the EAS operator 21. In a second embodiment, the observer 11 or the EAS operator 21 affirmatively commands a location determination (LD) system 31 and associated controller 33, which are connected to and located adjacent to the telephone 17, to determine and transmit the present location of the LD system to the EAS operator 21.

The present location of the phone 17 is determined by the LD system 31, including an LD signal antenna and LD signal receiver/processor, whose associated inaccuracy is preferably no more than 10–20 meters (M). One such LD system 31 is a Satellite Positioning System (SATPS), such as a Global Positioning System (GPS) or a Global Orbiting Navigational Satellite System (GLONASS). Details of an SATPS, a GPS and a GLONASS are given below. Another such LD system is an FM subcarrier system, such as disclosed by Kelley et al in U.S. Pat. No. 5,173,710, entitled "Navigation and Positioning System and Method Using, uncoordinated Beacon Signals", incorporated by reference herein. A third such LD system is a hybrid LD system that combines an SATPS and a FM subcarrier system, as disclosed in U.S. patent application Ser. No. 08/171,557, entitled "Hybrid Location Determination System" and assigned to the assignee of this application.

As illustrated in FIG. 1, an SATPS includes a plurality of SATPS satellites 41, 43, 45, 47 travelling in coordinated, non-geosynchronous orbits and transmitting differently coded SATPS signals that are received by at least one mobile SATPS antenna 48 located on or near the Earth's surface. The SATPS antenna 48 is connected to an SATPS receiver/processor 49 that receives and processes the SATPS signals from the antenna and determines the present location of the antenna. An SATPS is a global LD system that provides adequate signals for determining the present location coordinates and/or receiver clock offset and/or velocity coordinates of the SATPS antenna 48. Use of an SATPS for location determination is discussed in more detail below.

Figure 2:
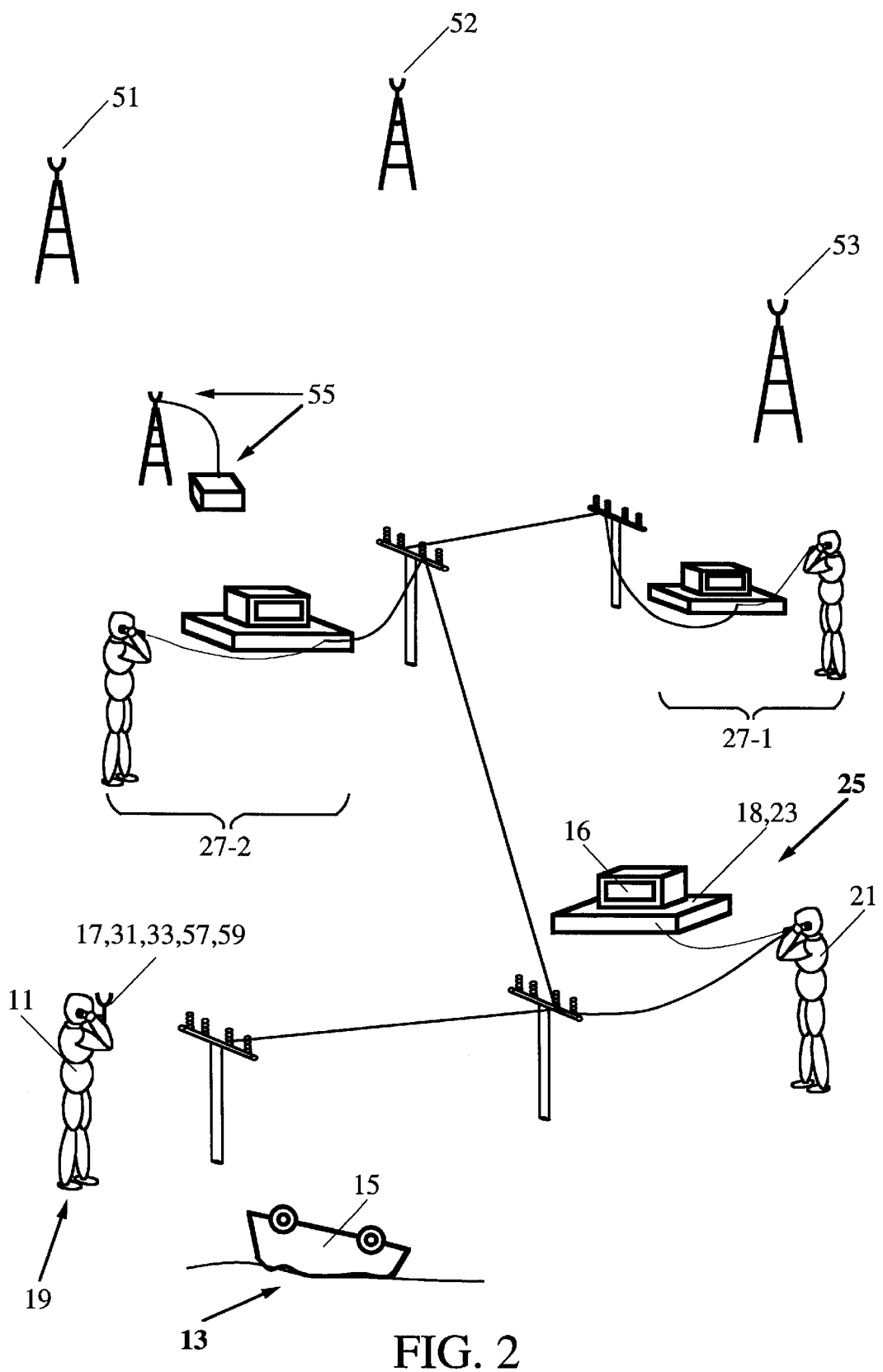

As illustrated in FIG. 2, an FM subcarrier system includes a plurality of at least three antenna sources 51, 52, 53 of FM subcarrier signals with fixed, known locations and a phase-determining transceiver/processor 55 for radiowaves whose spatial location is known and preferably (but not necessarily) fixed relative to the FM subcarrier sources 51, 52, 53. The FM subcarrier system also includes a mobile FM subcarrier signal antenna 57 and FM subcarrier signal receiver/processor 59 that is connected to the antenna 57. The FM subcarrier antenna sources 51, 52, 53 broadcast FM subcarrier signals whose phases relative to each other are usually unknown. These FM subcarrier signals are received by the transceiver/processor 55, which determines these relative phases using this transceiver's knowledge of its own location relative to the locations of the FM subcarrier antenna sources 51, 52, 53. The transceiver/processor 55 then broadcasts the values of these relative phases. The FM subcarrier signals broadcast by the sources 51, 52, 53 and the relative phase information broadcast by the transceiver/processor 55 are received by the FM subcarrier signal antenna 57 and receiver/processor 59 and used to determine the present location of the antenna 57 by triangulation. Use of an FM subcarrier system for location determination is discussed in more detail below.

In a third version of the LD system, an SATPS and an FM subcarrier system form a combined LD system that determines the present location of the LD system. An algorithm selects the SATPS-determined location or the FM subcarrier system-based location, based upon comparison of a certain signal quality parameter for each of the two systems. This approach is discussed in detail in U.S. patent application Ser. No. 08/171,557, op. cit.

When the EAS operator 21 and the EAS system 23 in FIG. 1 or 2 receive the phone call and spatial location signal from the phone 17 used by the observer 11, the EAS response system 23 automatically displays an electronic map 16 in visually perceptible form from a database 18, showing the site 19 of the phone 17. The EAS operator 21 receives the basic descriptive information from the observer 11, determines the type of EA incident involved here, and causes the system to display the phone numbers (and, optionally, addresses and locations on the map) of the N available EAS responders 27-1, 27-2, . . . , 27-N for that type of EA incident who are likely to be able to reach the emergency site 13 in the shortest time interval. Here, N is a positive integer, such as 1, 2, 3 or 4.

The length of a time interval $\Delta t$(response) required for a given EAS responder 27-$n$ to reach the observer's site 19 or the nearby emergency site 13 may be determined by dividing the Euclidean distance between that responder's home office and the target site by an estimated average velocity at which a responder's vehicle can move from the responder's site 21 to the emergency site 13. Alternatively and preferably, the EAS system 23 can more accurately estimate $\Delta t$(response) by (1) determining a most likely route from the responder's home office to the target site, (2) decomposing this route into linear or curvilinear segments, (3) estimating the time required for the responder's vehicle to move along each route segment, and (4) adding the times required to move along each segment. The EAS system can select the most likely route used by an EAS responder by computing the estimated response time value $\Delta t$(response) for two or more competing routes and selecting the route with the smallest estimated value $\Delta t$(response).

The EAS operator 21 queries one or more of these N EAS responders, determines which EAS responder, 27-F, is available and is likely to be able to reach the emergency site 13 most quickly, and assigns the EAS responder 27-F to respond to the EAS incident at the site 13. Preferably, the EAS operator 21 informs the EAS responder 27-F of the general and special equipment and/or generally and specially trained personnel that may be needed for adequate response to this EAS incident, before the EAS responder 27-F departs for the emergency site 13.

Optionally, the electronic map 16 or another visual display can display a list of general equipment, special equipment, general training and/or special training that may be needed at the emergency site, when the type of EA incident is determined. FIGS. 3A, 3B, 3C and 3D illustrate suitable displays of general and special equipment and personnel training that might be needed to respond, respectively, to an emergency involving (1) a structure fire, (2) a vehicle accident with injuries, (3) a shooting or other intentional or non-intentional injury, (4) a naturally occurring disaster, such as a tornado or earthquake. Optionally, the map 16 and/or these displays can be patched through for use by the responders 27-$n$.

The EAS operator 21 can then verbally advise the candidate EAS responders of the needs at the site or can electronically transmit a list of these needs to each of the candidate EAS responders, by activating selective switches on or associated with the list display. Each candidate EAS responder can then determine if it is "qualified"; that is, if it is (1) available and (2) has the equipment and trained personnel required to respond to the incident at the site 13. This avoids a situation where the chosen EAS responder vehicle 28-F arrives at the emergency site 13 with less than all the equipment and/or trained personnel needed for this response.

Unless the EAS incident clearly calls for response by more than one EAS responder, the EAS operator 21 will assign only one EAS responder for this incident. This avoids a situation where several responders arrive at an emergency site 13 but only one is required.

After the EAS responder vehicle 28-F has departed for the emergency site 13, but before or at about the estimated time the EAS responder vehicle will arrive at this site, the EAS operator 21 and the assigned EAS responder vehicle communicate with each other to verify that the assigned EAS responder vehicle will, in fact, arrive at the emergency site 13. If, for whatever reason, the assigned EAS responder vehicle 28-F cannot reach the emergency site 13 (e.g., because of blocked access, an accident involving the responder vehicle 28-$n$, or other reasons), the EAS operator 21 will promptly assign another EAS responder 27-$n$ (n≠F) to respond to the emergency site 13, as illustrated in FIG. 8.

One approach for this verification is to monitor the present location of the assigned EAS responder. Each assigned EAS responder 27-F is assigned a distinguishable indicium, and this indicium appears on the map 16 used by the EAS operator 21 after that responder is assigned to respond to the incident at the site 13. The assigned EAS responder vehicle 28-F carries an LD system 29-F and a transmitter and LD system-transmitter controller or interface, referred to collectively here as an "EAS responder LD system." The EAS responder LD system is activated when the assigned EAS responder vehicle begins moving toward the emergency site, and the controller or interface causes the EAS responder LD system to determines its own location and to transmit this location to the EAS system 23, for display as a (moving) indicium location on the EAS operator map 16. The indicium representing the EAS responder LD system is now observed to move, on the map 16, toward the observer's site 19 or the nearby emergency site 13. If the EAS operator 21 or the EAS system 23 subsequently determines that the EAS responder LD system is no longer moving toward the the site 19 or the site 13, the EAS operator 21 can contact this EAS responder and determine whether an alternate EAS responder should be assigned to respond to the emergency.

Figure 4:
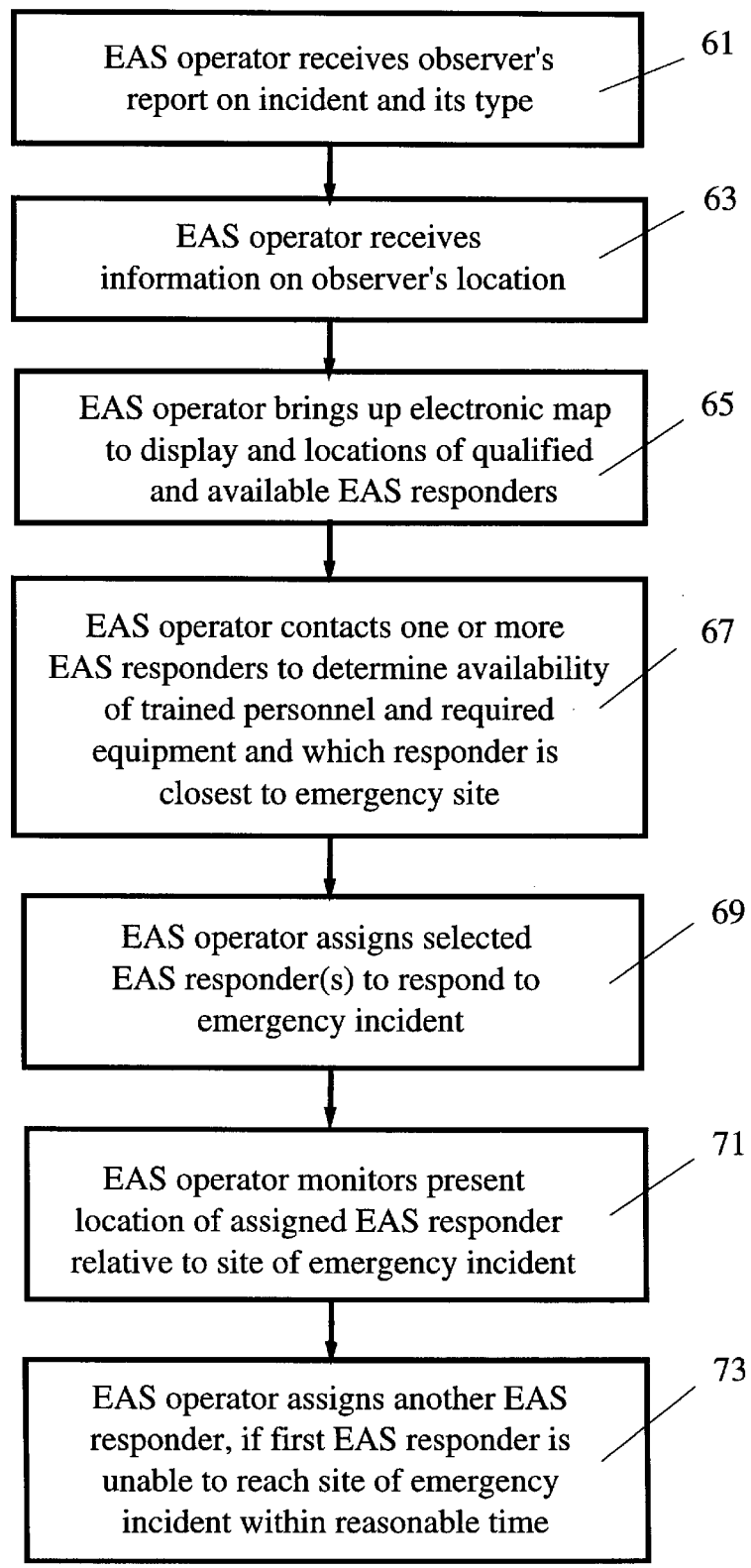
FIG. 4 is a flow chart of a procedure for receiving and responding to 911 or other EAS calls according to the invention.

FIG. 4 is a flow chart illustrating a procedure for practising the invention. In step 61, an observer of an emergency event reports the incident to an EAS operator, using a telephone. As the observer reports the incident and incident type to the EAS operator (step 61), the EAS operator also receives information on the observer's location from an LD system associated with the phone used by the observer, in step 63. In step 65, an electronic map, showing the observer's phone location and the location and phone numbers of any nearby and available EAS responders, appears on a screen, for use by the EAS operator. In step 67, the EAS operator contacts one or more of the suitable and available EAS responders, indicates the type of emergency and present location of the observer (or of the emergency site, if known), and determines which available EAS responder (1) has the required equipment and trained personnel to properly respond to the emergency and (2) is closest to the observer's present location or emergency site. In step 69, the EAS operator assigns the available EAS responder satisfying both of the requirements (1) and (2) to respond to the emergency event. In step 71 (optional), the EAS operator subsequently monitors the present location of the EAS responder assigned to respond to the emergency. In step 73 (optional), if the assigned EAS responder is unable to reach the emergency site within a reasonable time interval, the EAS operator assigns another EAS responder to respond to the emergency.

Figure 5:
FIG. 5 illustrates a conventional phone connected to an LD system.

The telephone used by the observer 11 in FIGS. 1 and 2 to place the call to the EAS operator 21 may be a conventional telephone 81, as illustrated in FIG. 5, with an LD module 83, connected to the telephone 81 through an controller/interface 85. For a stationary telephone, the LD module 83 may be a simple memory module that holds the (fixed) location of this telephone (expressed in suitable two-dimensional or three-dimensional location coordinates), where the memory can be queried and caused to disclose this phone location through use of the controller/interface 85. The observer uses this phone 81 in a conventional manner to contact the EAS operator and to explain the nature of the emergency incident. The observer or the EAS operator then activates the controller/interface 85 to cause the location of the phone 81 to be transmitted over the telephone channel to the EAS operator, for display and subsequent use.

Figure 6:
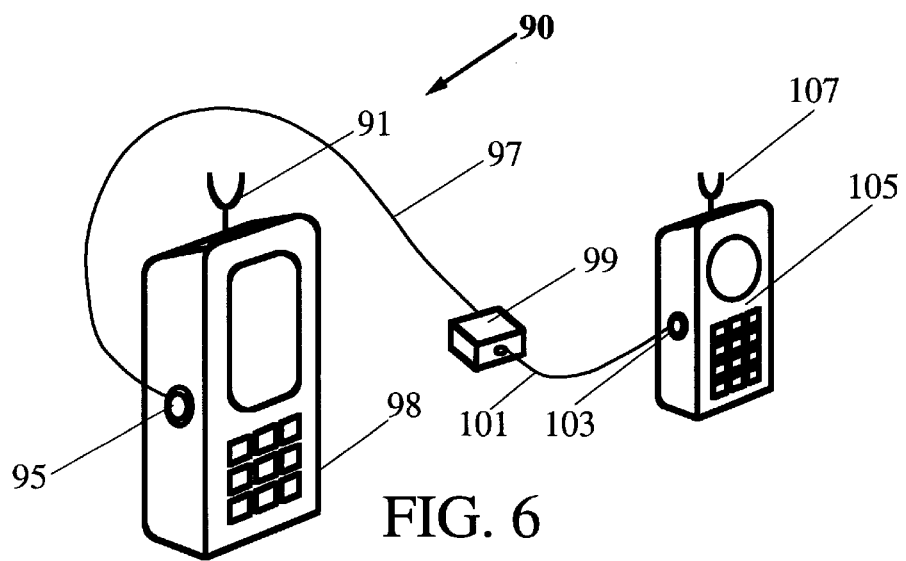
FIGS. 6 and 7 illustrate suitable LD system and cellular phone modules that can be used to practice the invention.

FIG. 6 illustrates suitable LD system and cellular phone modules that can be used by the observer 11 in FIGS. 1 and 2. In FIG. 6, an LD system 90, including an LD signal antenna 91 and LD signal receiver/processor 93, is connected at a port or jack 95 through a cable or wire 97, through a modem 99, and through another cable or wire 101 to a port or jack 103 for a cellular telephone 105. The cellular telephone has an antenna 107 for radiowave communication with the EAS operator.

The LD system 90 can be an SATPS LD system, an FM subcarrier LD system, a hybrid of these two systems, or a ground-based LD system such as Loran-C, Tacan, Omega, Decca, JTIDS or PLRS. The cellular telephone 105 can be, for example, a digital data ready cellular phone, such as the OKI 1150, the AT&T 3850, the Audiovox MVX700, the Technophone MC901, or some other cellular phone that has a port or jack 103 that accepts cable or wire transmissions. The cellular phone 105 in FIG. 6 can be replaced by a "walkie-talkie" or by a Specialty Mobile Radio (SRM) that is patched to a public switched telephone network (PSTN), and then to the EAS operator.

Figure 7:
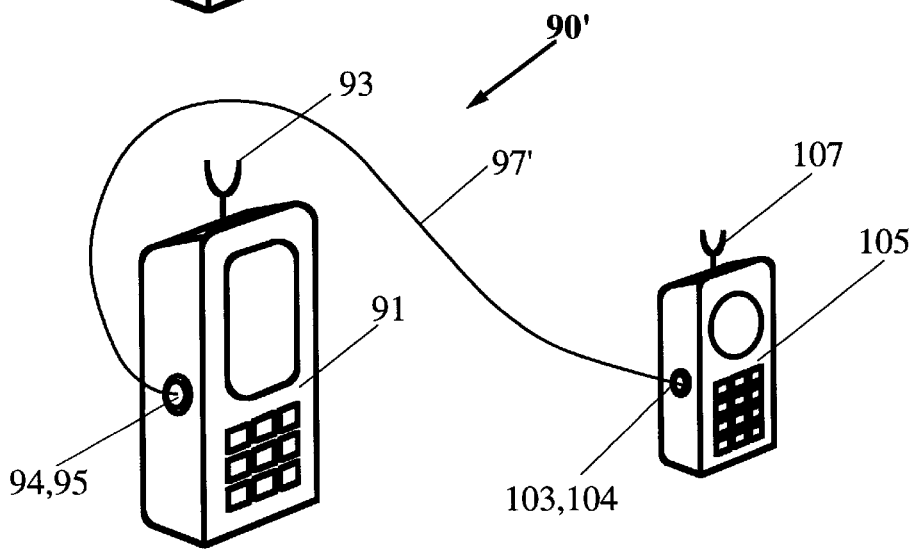

Alternatively, the LD system 90' or the cellular telephone 105' can have a built-in modem for signal transmission, as illustrated in FIG. 7. In this situation, a simple cable or wire 97' is connected to the ports or jacks of the LD system (94, 95) or of the cellular phone (103, 104).

A cellular phone can transmit its present spatial location coordinates on a standard voice channel, using occasional breaks in voice signals to transmit this as a modest amount of analog or digital information, or imposing breaks in the normal voice signals to transmit this information in a data-over-voice approach.

Alternatively, a cellular phone can transmit this location information on a little-used cellular telephone control channel that is occasionally used for other purposes. This information would include an indicium indicating the intended recipient (EAS operator) of the information and would be initially received by a mobile cellular telephone switching office (MCTSO); the MCTSO would then promptly route this information to the EAS operator, for use in determining the present location of the observer who is reporting the emergency incident. This present location information need only be transmitted and received once so that continuing transmission is not required here.

An SATPS location determination (LD) system includes three or more satellite signal transmitters, with receivers located on the Earth's surface or adjacent to the Earth's surface, that transmits information from which an observer's present location and/or the time of observation can be determined. Two operational systems, each of which qualifies as an SATPS, are the Global Positioning System and the Global Orbiting Navigational System.

The Global Positioning System (GPS) is part of a satellite-based navigation system developed by the United States Defense Department under its NAVSTAR satellite program. A fully operational GPS includes up to 24 satellites approximately uniformly dispersed around six circular orbits with four satellites each, the orbits being inclined at an angle of 55° relative to the equator and being separated from each other by multiples of 60° longitude. The orbits have radii of 26,560 kilometers and are approximately circular. The orbits are non-geosynchronous, with 0.5 sidereal day (11.967 hours) orbital time intervals, so that the satellites move with time relative to the Earth below. Theoretically, three or more GPS satellites will be visible from most points on the Earth's surface, and visual access to two or more such satellites can be used to determine an observer's position anywhere on the Earth's surface, 24 hours per day. Each satellite carries a cesium or rubidium atomic clock to provide timing information for the signals transmitted by the satellites. Internal clock correction is provided for each satellite clock.

Each GPS satellite transmits two spread spectrum, L-band carrier signals: an L1 signal having a frequency $f1=1575.42$ MHz and an L2 signal having a frequency $f2=1227.6$ MHz. These two frequencies are integral multiples $f1=1540 f0$ and $f2=1200 f0$ of a base frequency $f0=1.023$ MHz.

The L1 signal from each satellite is binary phase shift key (BPSK) modulated by two pseudo-random noise (PRN) codes in phase quadrature, designated as the C/A-code and P-code. The L2 signal from each satellite is BPSK modulated by only the P-code. The nature of these PRN codes is described below.

One motivation for use of two carrier signals L1 and L2 is to allow partial compensation for propagation delay of such a signal through the ionosphere, which delay varies approximately as the inverse square of signal frequency f (delay $f^{-2}$). This phenomenon is discussed by MacDoran in U.S. Pat. No. 4,463,357, which discussion is incorporated by reference herein. When transit time delay through the ionosphere is determined, a phase delay associated with a given carrier signal can be determined.

Use of the PRN codes allows use of a plurality of GPS satellite signals for determining an observer's position and for providing navigation information. A signal transmitted by a particular GPS signal is selected by generating and matching, or correlating, the PRN code for that particular satellite. All PRN codes are known and are generated or stored in GPS satellite signal receivers carried by ground observers. A first PRN code for each GPS satellite, sometimes referred to as a precision code or P-code, is a relatively long, fine-grained code having an associated clock or chip rate of $10 f0=10.23$ MHz. A second PRN code for each GPS satellite, sometimes referred to as a clear/acquisition code or C/A-code, is intended to facilitate rapid satellite signal acquisition and hand-over to the P-code and is a relatively short, coarser-grained code having a clock or chip rate of $f0=1.023$ MHz. The C/A-code for any GPS satellite has a length of 1023 chips or time increments before this code repeats. The full P-code has a length of 259 days, with each satellite transmitting a unique portion of the full P-code. The portion of P-code used for a given GPS satellite has a length of precisely one week (7.000 days) before this code portion repeats. Accepted methods for generating the C/A-code and P-code are set forth in the document GPS Interface Control Document ICD-GPS-200, published by Rockwell International Corporation, Satellite Systems Division, Revision B-PR, Jul. 3 1991, which is incorporated by reference herein.

The GPS satellite bit stream includes navigational information on the ephemeris of the transmitting GPS satellite and an almanac for all GPS satellites, with parameters providing corrections for ionospheric signal propagation delays suitable for single frequency receivers and for an offset time between satellite clock time and true GPS time. The navigational information is transmitted at a rate of 50 Baud. A useful discussion of the GPS and techniques for obtaining position information from the satellite signals is found in Tom Logsdon, *The NAVSTAR Global Positioning System*, Van Nostrand Reinhold, New York, 1992, pp. 1–90.

A second configuration for global positioning is the Global Orbiting Navigation Satellite System (GLONASS), placed in orbit by the former Soviet Union and now maintained by the Russian Republic. GLONASS also uses 24 satellites, distributed approximately uniformly in three orbital planes of eight satellites each. Each orbital plane has a nominal inclination of 64.8° relative to the equator, and the three orbital planes are separated from each other by multiples of 120° longitude. The GLONASS circular orbits have smaller radii, about 25,510 kilometers, and a satellite period of revolution of $8/17$ of a sidereal day (11.26 hours). A GLONASS satellite and a GPS satellite will thus complete 17 and 16 revolutions, respectively, around the Earth every 8 days. The GLONASS system uses two carrier signals L1 and L2 with frequencies of $f1=(1.602+9k/16)$ GHz and $f2=(1.246+7k/16)$ GHz, where k $(=0, 1, 2, \ldots, 23)$ is the channel or satellite number. These frequencies lie in two bands at 1.597–1.617 GHz (L1) and 1,240–1,260 GHz (L2). The L1 code is modulated by a C/A-code (chip rate=0.511 MHz) and by a P-code (chip rate=5.11 MHz). The L2 code is presently modulated only by the P-code. The GLONASS satellites also transmit navigational data at at rate of 50 Baud. Because the channel frequencies are distinguishable from each other, the P-code is the same, and the C/A-code is the same, for each satellite. The methods for receiving and analyzing the GLONASS signals are similar to the methods used for the GPS signals.

Reference to a Satellite Positioning System or SATPS herein refers to a Global Positioning System , to a Global Orbiting Navigation System, and to any other compatible satellite-based system that provides information by which an observer's position and the time of observation can be determined, all of which meet the requirements of the present invention.

A Satellite Positioning System (SATPS), such as the Global Positioning System (GPS) or the Global Orbiting Navigation Satellite System (GLONASS), uses transmission of coded radio signals, with the structure described above, from a plurality of Earth-orbiting satellites. A single passive receiver of such signals is capable of determining receiver absolute position in an Earth-centered, Earth-fixed coordinate reference system utilized by the SATPS.

A configuration of two or more receivers can be used to accurately determine the relative positions between the receivers or stations. This method, known as differential positioning, is far more accurate than absolute positioning, provided that the distances between these stations are substantially less than the distances from these stations to the satellites, which is the usual case. Differential positioning can be used for survey or construction work in the field, providing location coordinates and distances that are accurate to within a few centimeters.

In differential position determination, many of the errors in the differential SATPS that compromise the accuracy of absolute position determination are similar in magnitude for stations that are physically close. The effect of these errors on the accuracy of differential position determination is therefore substantially reduced by a process of partial error cancellation.

An SATPS antenna receives SATPS signals from a plurality (preferably four or more) of SATPS satellites and passes these signals to an SATPS signal receiver/processor, which (1) identifies the SATPS satellite source for each SATPS signal, (2) determines the time at which each identified SATPS signal arrives at the antenna, and (3) determines the present location of the SATPS antenna from this information and from information on the ephemerides for each identified SATPS satellite. The SATPS signal antenna and signal receiver/processor are part of the user segment of a particular SATPS, the Global Positioning System, as discussed by Tom Logsdon, op cit.

The FM subcarrier location determination (LD) system includes three or more spaced apart FM signal transmitters, operating with a subcarrier frequency displaced from the carrier frequency $f_c$ by ±19 kHz or a multiple thereof, with each FM transmitter being positioned at fixed, known locations, such as nearby FM radio stations. The system also includes a portable FM subcarrier signal antenna and receiver/processor, located at the user whose location is to be determined, that receives and analyzes the FM subcarrier signals and determines the location of the FM antenna at selected times. The FM subcarrier signals can be received at substantially all locations outside or inside a building or structure, if the FM subcarrier signal transmitter is within a selected distance of no more than about 50 km from the FM antenna. Each of the transmitted FM subcarrier signals has an associated phase that may be known initially but that may change from time to time. The transmitted FM signals are also received by an FM reference station with fixed, known location that determines the phase differences of these FM signals and transmits to the user FM phase information signals that indicate these FM subcarrier signal phase differences. Optionally, the FM reference station may also act as a source of, and transmit its own, FM subcarrier signals, and the FM phase information signals may include the phase difference between the FM reference station subcarrier signal and at least one of the other FM subcarrier signals transmitted by another FM subcarrier signal source. In this instance, the FM reference station transmitter antenna should be spaced apart from a plane defined by the locations of the transmitter antennas for the other three FM subcarrier signal sources.

An FM subcarrier LD system may operate in a manner disclosed by Kelley et al in U.S. Pat. No. 5,173,710. This system allows determination of an absolute location of a vehicle. FM subcarrier signals are received from three radio stations with known locations but unknown relative phases by signal processors at the vehicle and at a fixed station with known location relative to the three radio stations. The fixed station processor determines the relative phases of the three radio stations FM subcarrier signals and broadcasts this relative phase information to the vehicle. The vehicle processor receives this relative phase data and determines its absolute location, using the phases of the FM signals it senses at its own location.

We claim:

1. A method for responding to occurrence of an emergency event, the method comprising the steps of:

receiving, by an emergency assistance services operator, denoted an "EAS" operator, information on an emergency event observed by an observer and on location of the observer, where the observer location is automatically determined and transmitted to the EAS operator;

displaying for the EAS operator the observer location and a location of at least one site of an EAS responder that provides emergency assistance services and that is available to respond to the emergency event;

estimating a time interval Δt(response) required for at least one available EAS responder to move from at least one EAS responder site to the observer location;

estimating which EAS responder will take the shortest time interval Δt(response) to reach the observer location, and selecting and notifying at least one EAS responder to respond to the emergency event;

receiving information on a present location of a selected EAS responder vehicle dispatched by the selected EAS responder to the observer location;

determining whether the selected EAS responder vehicle will reach the observer location within a selected time interval; and when it is determined that the selected EAS responder vehicle will not reach the observer location within the selected time interval, selecting and notifying a second EAS responder to respond to the emergency event.

2. The method of claim 1, wherein said step of receiving said observer location comprises the steps of:

receiving location determination signals, denoted "LD" signals, at an LD signal module that is positioned adjacent to said observer, and using the LD signals to determine the location of the LD signal module; and using a communication channel, which is separate from a communication channel used by said observer to report said emergency event to said EAS operator, to report the location of the LD signal module to said EAS operator.

3. The method of claim 2, wherein said step of receiving said location of said LD signal module comprises the step of:

when said observer observes said emergency event, receiving a cellular telephone transmission from said observer, by said EAS operator, concerning said emergency event and said observer location.

4. The method of claim 3, further comprising the step of transmitting said observer location information on a signal-carrying channel used to carry voice signals between a cellular telephone used by said observer and said telephone used by said EAS operator.

5. The method of claim 3, further comprising the step of transmitting said observer location information on a signal-carrying channel that is not used to carry voice signals between a cellular telephone used by said observer and said telephone used by said EAS operator.

6. The method of claim 1, further comprising the steps of:

obtaining, for use by said EAS operator, a statement of selected equipment, if any, that is required to respond to said emergency event; and determining whether at least one available EAS responder has the selected equipment to respond to said emergency event.

7. The method of claim 6, wherein said step of determining what selected equipment is required to respond to said emergency event comprises the step of choosing said selected equipment from emergency response equipment drawn from the class consisting of: fire fighting equipment, self-contained breathing apparatus, a gurney for transporting an injured person, a source of oxygen, a source of whole blood for an injured person, and first aid equipment for an injured person.

8. The method of claim 1, further comprising the steps of:

obtaining, for use by said EAS operator, a statement of EAS responder personnel training, if any, that is required to respond to said emergency event; and determining whether at least one available EAS responder has at least one person with the selected personnel training to respond to said emergency event.

9. The method of claim 1, wherein said step of estimating said length Δt(response) comprises the steps of:

determining the location coordinates of said observer location and the location coordinates of said at least one EAS responder site;

determining the Euclidean distance D between said observer location and said at least one EAS responder site;

estimating an average velocity v at which an EAS responder vehicle can travel in moving from said at least one EAS responder site to said observer location; and estimating said length Δt(response) of the time interval required for said selected EAS responder vehicle to respond to said emergency event as approximately a ratio D/v.

10. The method of claim 1, wherein said step of estimating said length Δt(response) comprises the steps of:

determining at least one likely route for said selected EAS responder vehicle to follow in moving from said EAS responder site to said observer location;

decomposing at least one of the likely routes into a sequence of at least two route segments, numbered k=1, 2, . . . , with each route segment including a portion of a road that is not included in any other route segment;

estimating an average velocity v(k) at which said selected EAS responder vehicle can travel along each route segment number k, and estimating the length L(k) of each route segment number k;

estimating a length of time Δt(k) required for said selected EAS responder vehicle to travel along a route segment number k; and estimating said length Δt(response) of the time interval required for said selected EAS responder vehicle to respond to said emergency event as the sum over the index k of the lengths of time Δt(k).

11. The method of claim 10, wherein said step of estimating said length of time Δt(k) required for said selected EAS responder vehicle to travel along said route segment number k comprises the step of setting said length of time Δt(k) equal to a ratio L(k)/v(k).

12. The method of claim 1, further comprising the step of using as said LD signal module a Satellite Positioning System (SATPS) module that comprises an SATPS signal antenna and an SATPS signal receiver/processor connected to the SATPS signal antenna, where the SATPS signal antenna and SATPS signal receiver/processor receive signals from a plurality of SATPS satellites and determine the position of the SATPS signal antenna from analysis of these signals.

13. The method of claim 1, further comprising the step of using as said LD signal module an FM subcarrier module that comprises:

a first FM subcarrier receiver to receive FM subcarrier signals from at least three spaced apart transmitters of FM subcarrier signals, and from a second receiver of FM subcarrier signals that receives the FM subcarrier signals from the FM subcarrier signal transmitters, determines the relative phases of these three FM subcarrier signals, and transmits information on these relative phases, with each FM transmitter having a known location; and where the first receiver receives the FM subcarrier signals transmitted by the FM subcarrier signal transmitters, receives the relative phase information from the second receiver, and determines the location of the first receiver.

14. The method of claim 1, wherein said step of receiving information on said present location of said selected EAS responder vehicle comprises the steps of:

receiving location determination signals, denoted "LD" signals, from a plurality of LD signal sources at an LD signal module that is carried in or on said selected EAS responder vehicle, and determining and issuing said present location of said selected EAS responder vehicle from the LD signals, where the LD signal module is connected to a cellular telephone that is carried in or on said selected EAS responder vehicle; and receiving said location of said selected EAS responder vehicle at a cellular telephone, which is connected to the LD signal module, and using the cellular telephone to communicate said location of said selected EAS responder vehicle to said EAS operator at a plurality of selected times as said selected EAS responder vehicle moves generally in a direction toward said observer location.

15. Apparatus for responding to occurrence of an emergency event, the apparatus comprising:

a telephone, monitored by an emergency assistance service operator, denoted an "EAS" operator, for receiving, from an observer of an emergency event, information on the type of emergency event and location of the observer, where the observer location is automatically determined and transmitted to the EAS operator;

a response module connected to the telephone and comprising:

an electronic display that displays, for the EAS operator, the observer location and a location of at least one site of an EAS responder that provides emergency assistance services and that is available to respond to the emergency event; and a computer that: (1) receives information on the observer location and on at least one EAS responder site location; (2) estimates a time interval length Δt(response) required for at least one available EAS responder to move from an EAS responder site to the observer location; (3) estimates which EAS responder will take the shortest time interval Δt(response) to reach the observer location; (4) selects and notifies at least one EAS responder to respond to the emergency event; (5) receives information on a present location of an EAS responder vehicle dispatched by the selected EAS responder to the observer location; (6) determines whether the selected EAS responder vehicle will reach the observer location within a selected time interval; and (7) when it is determined that the selected EAS responder vehicle will not reach the observer location within the selected time interval, the computer selects and notifies a second EAS responder to respond to the emergency event.

16. The apparatus of claim 15, wherein said response module provides information on selected equipment that is required to respond to said emergency event and determines whether at least one of said EAS responders has the selected equipment required to respond to said emergency event.

17. The apparatus of claim 15, wherein said response module provides information on selected personnel training that is required to respond to said emergency event and determines whether at least one of said EAS responders has at least one person with the selected training required to respond to said emergency event.

18. The apparatus of claim 15, wherein said telephone uses a communication channel, which is separate from a communication channel used by said observer to report said emergency event to said EAS operator, to receive information on said location of said observer.

19. The apparatus of claim 15, wherein said computer estimates said time length Δt(response) by:

determining the location coordinates of said observer location and the location coordinates of said at least one EAS responder site;

determining the Euclidean distance D between said observer location and said at least one EAS responder site;

estimating an average velocity v at which an EAS responder vehicle can travel in moving from said at least one EAS responder site to said location of said observer; and estimating said length of time Δt(response) of the time interval required for said selected EAS responder vehicle to respond to said emergency event as approximately a ratio D/v.

20. The apparatus of claim 15, wherein said computer estimates said time length Δt(response) by:

determining at least one likely route for said selected EAS responder vehicle to follow in moving from said EAS responder site to said observer location;

decomposing at least one of the likely routes into a sequence of at least two route segments, numbered k=1, 2, ..., with each route segment including a portion of a road that is not included in any other route segment;

estimating an average velocity v(k) at which said selected EAS responder vehicle can travel along each route segment number k, and estimating the length L(k) of each route segment number k;

estimating a length of time Δt(k) required for said selected EAS responder vehicle to travel along a route segment number k; and estimating said length of time Δt(response) of the time interval required for said selected EAS responder vehicle to respond to said emergency event as the sum over the index k of the lengths of time Δt(k).

* * * * *